US 009754404B2

United States Patent
Graumann et al.

(10) Patent No.: US 9,754,404 B2
(45) Date of Patent: Sep. 5, 2017

(54) METHOD FOR GENERATING DISPLAY IMAGE DATA

(71) Applicant: SIEMENS HEALTHCARE GMBH, Erlangen (DE)

(72) Inventors: Rainer Graumann, Hoechstadt (DE); Gerhard Kleinszig, Forchheim (DE); Wei Wei, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 403 days.

(21) Appl. No.: 14/277,227

(22) Filed: May 14, 2014

(65) Prior Publication Data

US 2014/0340401 A1    Nov. 20, 2014

(30) Foreign Application Priority Data

May 14, 2013    (DE) .......................... 10 2013 208 793

(51) Int. Cl.
| | |
|---|---|
| *G06T 15/00* | (2011.01) |
| *G06T 15/08* | (2011.01) |
| *A61B 17/17* | (2006.01) |
| *A61B 6/12* | (2006.01) |
| *G06T 7/70* | (2017.01) |
| *A61B 6/00* | (2006.01) |

(52) U.S. Cl.
CPC ............... *G06T 15/08* (2013.01); *A61B 6/12* (2013.01); *A61B 6/5205* (2013.01); *A61B 6/5235* (2013.01); *A61B 17/1703* (2013.01); *G06T 7/70* (2017.01); *A61B 6/505* (2013.01); *G06T 2207/10081* (2013.01); *G06T 2207/30052* (2013.01)

(58) Field of Classification Search
CPC ............... G06T 15/08; G06T 7/004; G06T 2207/10081; G06T 2207/30052; A61B 6/12; A61B 6/505; A61B 6/5205; A61B 6/5235; A61B 17/1703
USPC .................................................. 345/419, 424
See application file for complete search history.

(56) References Cited

U.S. PATENT DOCUMENTS

| | | | | |
|---|---|---|---|---|
| 5,655,545 A | * | 8/1997 | Johnson | A61B 17/00234 128/898 |
| 7,961,934 B2 | * | 6/2011 | Thrun | G01B 21/20 382/107 |
| 8,165,660 B2 | * | 4/2012 | Pfister | A61B 6/12 378/205 |
| 8,298,289 B2 | * | 10/2012 | White | A61B 17/562 623/21.11 |

(Continued)

FOREIGN PATENT DOCUMENTS

DE    102010034918 A1    2/2012

*Primary Examiner* — Phu K Nguyen

(57) ABSTRACT

A method generates a 3D image data set of a volume to be examined, in which at least part of a foreign object is positioned. A set of 2D projection images is recorded, the image regions which present the foreign object are detected in at least two 2D projection images of the set. The image regions which present the foreign object are segmented in the at least two 2D projection images. A marking assigned to the segmented image regions is incorporated in the at least two 2D projection images. The 2D projection images, including the at least two 2D projection images having the incorporated markings, are used for the reconstruction of a 3D image data set containing the marking.

9 Claims, 2 Drawing Sheets

(56) References Cited

U.S. PATENT DOCUMENTS

| | | | | |
|---|---|---|---|---|
| 8,357,203 B2* | 1/2013 | White | ........... | A61B 17/562 |
| | | | | 623/14.12 |
| 8,457,720 B2* | 6/2013 | Leiblein | ........... | A61B 6/12 |
| | | | | 600/427 |
| 8,538,106 B2* | 9/2013 | Ibarz | ........... | G06T 7/0067 |
| | | | | 382/130 |
| 8,824,761 B2* | 9/2014 | Palma | ........... | G06T 7/0012 |
| | | | | 345/419 |
| 9,129,363 B2* | 9/2015 | Chen | ........... | G06T 7/0012 |
| 2012/0045105 A1 | 2/2012 | Engel | | |

* cited by examiner

METHOD FOR GENERATING DISPLAY IMAGE DATA

CROSS-REFERENCE TO RELATED APPLICATION

This application claims the priority, under 35 U.S.C. §119, of German application DE 10 2013 208 793.4, filed May 14, 2013; the prior application is herewith incorporated by reference in its entirety.

BACKGROUND OF THE INVENTION

Field of the Invention

The invention relates to a method for generating a 3D image data set of a volume to be examined, in which at least part of a foreign object, preferably an instrument or an implant, is positioned.

The closed repositioning and fixation of a bone fracture using a rotating drill wire, also referred to as a Kirschner wire, is one of the oldest methods for surgical treatment of fractures still in regular use today. Nowadays, an image assistance system is frequently used during the treatment. That means an x-ray with which the position and orientation of the drill wire after its insertion is checked is taken not only after completion of the treatment, but instead, a check to determine whether the insertion occurs as intended is carried out at the beginning and during the insertion of the drill wire on the basis of image data, which are reproduced on a display.

SUMMARY OF THE INVENTION

It is accordingly an object of the invention to provide a method for generating display image data that overcome the above-mentioned disadvantages of the prior art methods of this general type, which invention is based on the object of specifying an advantageous method for generating a 3D image data set.

The method serves for generating a 3D image data set of a volume to be examined, in which at least part of a foreign object, preferably a medical instrument or an implant, is positioned, and moreover for generating display image data based on a corresponding 3D image data set. The display image data are then displayed on a display screen preferably during a treatment of a patient, as a result of which a treating doctor is assisted in guiding a medical instrument or in the positioning of an implant by the presentation of the position and the orientation of the medical instrument or of the implant within the body of the patient to be treated.

First, a set of 2D projection images, which is generated according to the principle of digital volume tomography for example using a computer tomography (typically "cone beam computed tomography" in English-speaking regions), is established, and subsequently, in at least two 2D projection images, those image regions are identified or detected that present the instrument or at least parts of the instrument or the implant or at least parts of the implant. The image regions which are identified or detected thusly are subsequently subjected to segmentation, wherein the detection or identification and/or the segmentation take place either manually by an operator or by the treating doctor or else automated with the aid of an image recognition computer program product.

In the further progression, the segmented image regions in the 2D projection images are assigned a marking, wherein the marking is preferably incorporated in the corresponding 2D projection images. That is to say that, for example, the position of the tip of a scalpel in each 2D projection image is located and that a cross-type pictogram is inserted into each 2D projection image at the respective position. Alternatively, a virtual marking is also provided, at which the specific position of the tip of the scalpel within each 2D projection image is converted into a coordinate tuple which is then added as additional information to the data set of the 2D projection image.

Based on the thusly modified 2D projection images, a 3D image data set is then reconstructed. With respect to the previously mentioned example, this means that the position of the tip of the scalpel within the volume is estimated by the position of the tip being determined in a plurality of 2D projection images, whose projection directions relative to one another and relative to the volume to be examined are known. So instead of reconstructing the 3D image data set on the basis of the set of 2D projection images and determining the tip of the scalpel within this 3D image data set, detection takes place in at least two 2D projection images, which is typically easier to do, and a conclusion relating to the position of the tip of the scalpel within the volume and thus in the 3D image is drawn on the basis of the respectively determined position within the 2D projection images.

Provision is preferably made here for an edge or tip of the medical instrument or of the implant to be provided with a marking, such that it is more easily recognized by a treating doctor when displaying the display image data, that is to say for example also when directly displaying one of the 2D projection images, on a display screen.

Alternatively or additionally, a virtual extension of the instrument or of the implant in its longitudinal direction is incorporated as a marking in the 2D projection images. In particular if, as is preferred, the instrument is a drill wire or a Kirschner wire, this virtual extension, which is represented for example by a simple line which is distinguishable by its color, allows the direction in which the drill wire can be driven forward to be estimated. The treating doctor can thus simply estimate from first placement of the drill wire to a bone fragment whether the selected approach will result in the desired positioning by driving the drill wire forward. This virtual extension or trajectory thus functions as a target device or target assistance for the insertion of the drill wire. This principle can be applied even if slightly curved drill wires are used, as long as it is ensured that the virtual extension in all 2D projection images extends in a straight line and is preferably configured as a tangent, in particular as a slope tangent, on the drill wire tip. The virtual extension then represents, as it were, the slope of the curve profile given by the curved drill wire in the corresponding 2D projection image.

Since the method is intended preferably for generating display image data for an image assistance system during a treatment of a patient, a plurality of 2D projection image sets are prepared, preferably during treatment, with the aid of the method presented here. As part of the method for producing at least one 2D projection image set, 2D projection images of at least two scanning operations are preferably combined with one another.

If a 3D image data set has already been prepared during a treatment, it might under certain circumstances be sufficient to carry out a partial scan, that is to say an incomplete scan, as it were, of the volume to be examined, during a subsequent scanning operation, in which for example only a few 2D projection images are captured. The 2D projection images produced during such a partial scan then do not form a complete 2D projection image set and are thus not suitable for reconstructing, on the basis thereof, a 3D image data set. However, if the volume to be examined within the body of the patient has moved only slightly relative to the scanned volume and the instrument or the implant has shifted substantially only slightly, the 2D projection images produced during the partial scan suffice to ascertain the changed position and orientation of the instrument or of the implant, and the current reconstructed position and orientation of the instrument or of the implant is simply inserted into the previously reconstructed image. This ultimately means that the display image data which were produced on the basis of the 2D projection image set of a first scanning operation are displayed on the display screen, and that the segmented image regions are presented in a displaced manner based on the information obtained during the second scanning operation.

Other features which are considered as characteristic for the invention are set forth in the appended claims.

Although the invention is illustrated and described herein as embodied in a method for generating display image data, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Mutually corresponding parts have in each case the same reference signs in all figures.

Figure 1:
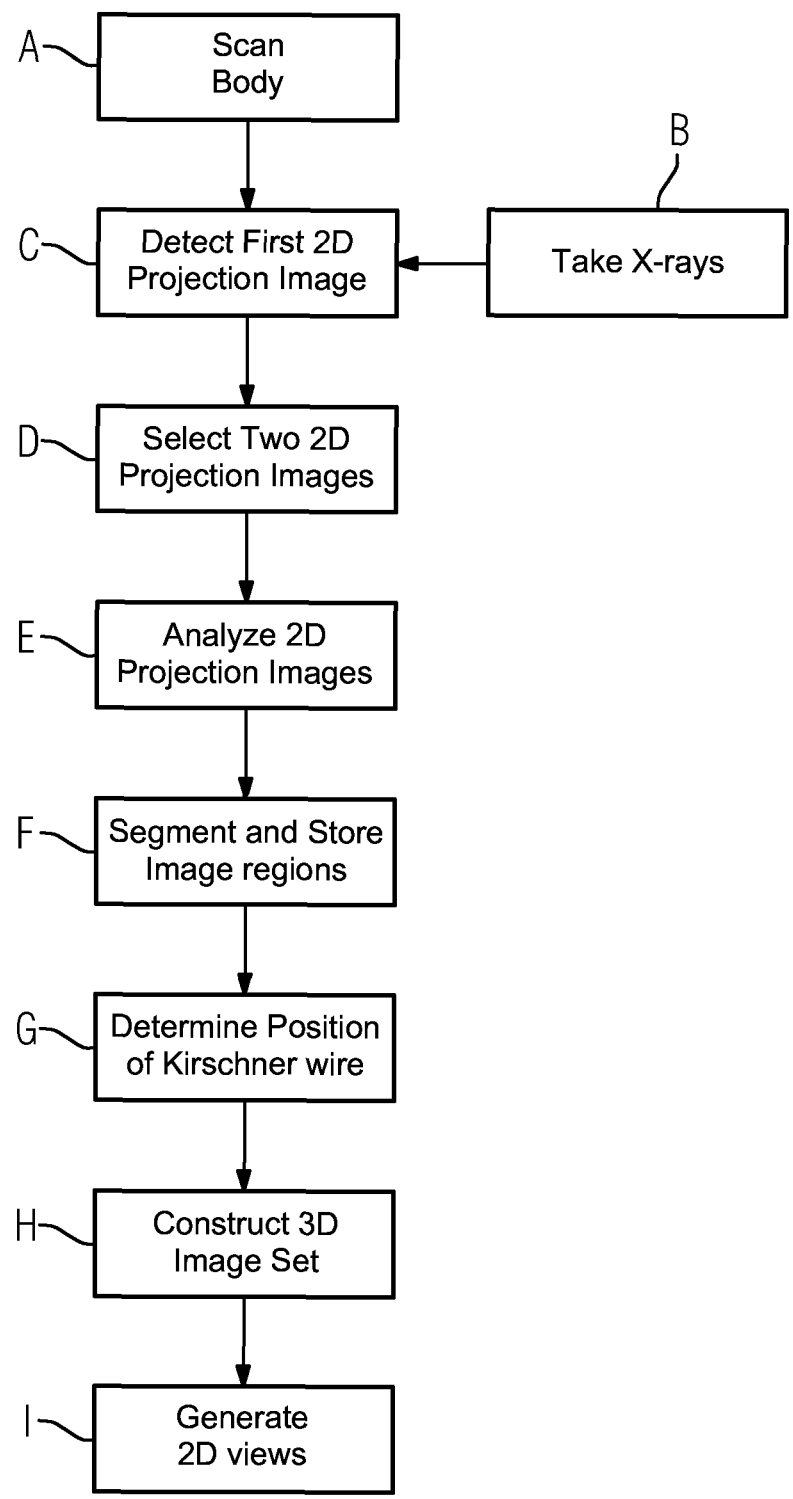
FIG. 1 is a block diagram of a method for generating display image data according to the invention.
Figure 2:
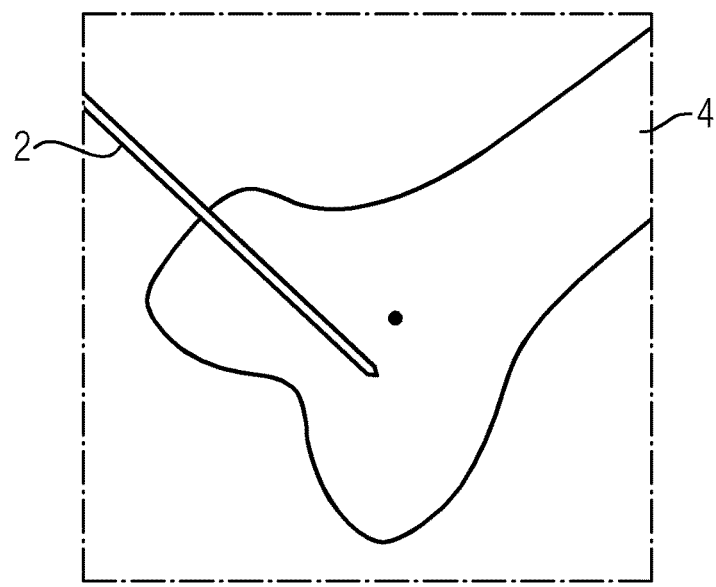
FIG. 2 is an x-ray projection image.

In the exemplary embodiment described below, a computer tomography (not illustrated in more detail) is adapted to carry out the method presented here for generating display image data, which is illustrated in FIG. 1 in a form of a block diagram. The computer tomography is used here in the treatment of a patient during which a Kirschner wire 2 is intended to be driven through one end of a bone 4. At the end of the treatment, the Kirschner wire 2 is intended to be disposed at a specified position and orientation within the bone 4, which is why the computer tomography is used in the treatment for image-assisted navigation during the guidance of the Kirschner wire 2 by a treating doctor.

To this end, a program stored in the computer tomography is started by an operator or by the treating doctor, wherein in a method step A, first the volume to be examined within the body of the patient, in which the bone 4 is located, is scanned, with a 2D projection image set being produced in the process.

In a method step C, the thusly produced 2D projection image set is detected as the first 2D projection image set of an order or sequence of 2D projection image sets and, in a method step D, two 2D projection images are selected from the 2D projection image set according to a specified criterion for post processing. In a method step E, the two selected 2D projection images are subsequently analyzed individually using image evaluation software, wherein those image regions in each selected 2D projection image that present parts of the Kirschner wire 2 are detected. The image regions are segmented in a method step F and stored in a separate data set at least temporarily in a memory.

In a further method step G, the position of the tip of the Kirschner wire 2 within each selected 2D projection image is determined and marked by the associated pixel coordinates being incorporated as additional information in the data set of each selected 2D projection image. The thusly prepared 2D projection image set is then utilized in a method step H for reconstructing a 3D image data set, wherein the position of the tip of the Kirschner wire 2 within the volume and thus in the 3D image data set is determined on the basis of the markings, that is to say the pixel coordinates, in the individual 2D projection images and on the basis of the known dependence of the projection directions of the 2D projection images relative to one another and relative to the volume to be examined within the body of the patient.

Finally, in a method step I, a 2D view, that is to say for example a projection presentation or a section presentation, and thus a set of display image data is generated on the basis of the 3D image data set with a marking, which set of display image data is then displayed on a display screen. The operator or the treating doctor can here, for example, change the viewing direction at any time, and, in accordance with the selection of the viewing direction, a corresponding set of display image data is generated on the basis of the 3D image data set with a marking.

Figure 3:
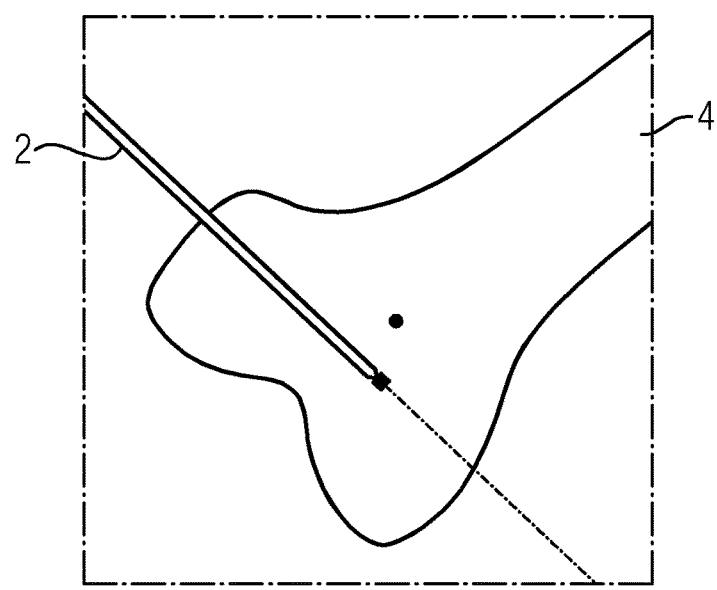
FIG. 3 is the x-ray projection image with a marking inserted.

In each 2D view, the position of the tip of the Kirschner wire 2, which results from the marking in the 3D image data set, is optically emphasized, specifically by showing a blue square at the position of the tip of the Kirschner wire 2 (in FIG. 3 a black square). In addition, a virtual extension of the Kirschner wire 2 in the longitudinal direction of the Kirschner wire 2 is, as a further marking, depicted by a blue line (in FIG. 3 by a dash-dot-dash line), such that the treating doctor can estimate on the basis of this in which direction the Kirschner wire 2 will move during driving forward.

At regular time intervals, the volume to be examined within the body of the patient is rescanned in a further scanning operation, as a result of which updated image information for the image-assisted treatment of the patient is obtained, such that the treating doctor can track the changes in orientation and position of the Kirschner wire 2 while driving the Kirschner wire 2 forward. In every other scanning operation, the volume to be examined is not scanned completely, and instead only individual x-rays are taken from a few directions in a method step B. The 2D projection images generated in the process consequently do not form a complete 2D projection image set and accordingly do not permit reconstruction of a complete 3D image data set either. They merely serve for the determination of the current orientation and position of the Kirschner wire 2, and, for the generation of display image data, the 2D projection images generated during a partial scanning of the volume to be examined are supplemented in a method step C by 2D projection images, generated during the respective previous scanning operation, of a complete 2D projection image set. Image data are thus substantially reproduced on the display screen, which are based, as it were, on an old 2D projection image set, wherein the segmented image regions of the 2D projection images are positioned at a changed, that is to say updated, position in the 2D projection images such that ultimately, an old view of the bone 4 and an old view of the Kirschner wire 2 can be seen on the display screen, wherein, however, the Kirschner wire 2 is presented with a current position and alignment relative to the bone 4.

The invention is not limited to the previously described exemplary embodiment. Instead, other variants of the invention can also be derived here from by the person skilled in the art without departing from the subject of the invention. In particular, all individual features described in connection with the exemplary embodiment are also combinable with one another in a different manner, without departing from the subject of the invention.

The following is a summary list of reference numerals and the corresponding structure used in the above description of the invention.

LIST OF REFERENCE SIGNS

2 Kirschner wire
4 bone
A method step A
B method step B
C method step C
D method step D
E method step E
F method step F
G method step G
H method step H
I method step I

The invention claimed is:

1. A method for generating a 3D image data set of a volume to be examined, in which at least part of a foreign object is positioned, which comprises the steps of:
   recording a set of 2D projection images;
   detecting image regions having the foreign object in at least two 2D projection images of the set of 2D projection images;
   segmenting the image regions having the foreign object in the at least two 2D projection images resulting in segmented image regions;
   incorporating a marking assigned to the segmented image regions in the at least two 2D projection images; and
   using the 2D projection images, including the at least two 2D projection images each having the marking, for a reconstruction of the 3D image data set containing the marking.

2. The method according to claim 1, which further comprises incorporating a further marking which accentuates a respective position of a tip of the foreign object in the 2D projection images.

3. The method according to claim 1, which further comprises incorporating a further marking which indicates a virtual extension of the foreign object in a longitudinal direction in the 2D projection images.

4. The method according to claim 1, wherein the foreign object is a drill wire.

5. The method according to claim 4, wherein the drill wire is a Kirschner wire.

6. The method according to claim 1, wherein the foreign object is a screw.

7. The method according to claim 1, which further comprises combining the 2D projection images of at least two scanning operations with one another for producing the set of 2D projection images.

8. The method according to claim 1, which further comprises combining the 2D projection images of at least two scanning operations with one another for producing the set of 2D projection images, wherein the volume to be examined is scanned in a first scanning operation using a computer tomography system, and the volume to be examined is partially scanned in a second scanning operation.

9. The method according to claim 1, wherein the foreign object is selected from the group consisting of instruments and implants.

\* \* \* \* \*